United States Patent [19]

Ellis

[11] 4,219,434
[45] Aug. 26, 1980

[54] HYDRAULIC FLUID COMPOSITIONS BASED ON MIXED GLYCOL ETHER-GLYCOL BORIC ACID ESTERS

[75] Inventor: James M. H. Ellis, Billingham, England

[73] Assignee: Imperial Chemical Industries Limited, London, England

[21] Appl. No.: 582,882

[22] Filed: Jun. 2, 1975

[30] Foreign Application Priority Data

Jun. 7, 1974 [GB] United Kingdom ............... 25342/74

[51] Int. Cl.$^2$ .............................................. C10M 3/48
[52] U.S. Cl. .................................................. 252/78.1
[58] Field of Search ................................. 252/78, 78.1

[56] References Cited

U.S. PATENT DOCUMENTS 3,925,223  12/1975  Coffman et al. ....................... 252/78

Primary Examiner—Harris A. Pitlick
Attorney, Agent, or Firm—Cushman, Darby & Cushman

[57] ABSTRACT

A hydraulic fluid comprises an ester of orthoboric acid of formula $CBA_2$ or $ABC_2$ in which C is a glycol residue and A is a glycol ether residue. The fluid may also contain a mono- or di-ether of a glycol.

15 Claims, No Drawings

HYDRAULIC FLUID COMPOSITIONS BASED ON MIXED GLYCOL ETHER-GLYCOL BORIC ACID ESTERS

The present invention relates to hydraulic fluids, in particular to hydraulic fluids containing an ester of boric acid.

According to the invention a hydraulic fluid comprises an ester of orthoboric acid of general formula

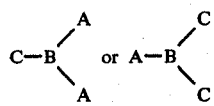

where C is a glycol residue, B is a boron atom and A is a glycol ether residue. By glycol residue we mean the radical remaining after one glycol hydroxyl group has been esterified by the boric acid, the other hydroxyl group being unreacted. Similarly the glycol ether residue is derived from the mono ether of a glycol, the free hydroxyl group of the mono ether being esterified by the boric acid, the ether group being unreacted.

The glycol which preferably contains up to 30 carbon atoms may be ethylene, propylene or butylene glycol, neopentyl glycol, or a polyglycol, i.e. a polyethylene or polypropylene glycol or a glycol derived from mixed ethylene oxide/propylene oxide units. The polyglycol contains for preference 2 to 20, more preferably 2 to 6 repeating ethylene oxide and/or propylene oxide units, e.g. tetraethylene glycol.

The glycol ether may be derived from any one of the glycols listed in the preceding paragraph and the ether group is preferably an alkyl ether group, e.g. a $C_1$ to $C_{20}$ alkyl group, particularly a lower ($C_1$ to $C_6$) alkyl group, e.g. an ethyl ether.

The borate ester may comprise 5 to 98% by weight of the hydraulic fluid composition, preferably 10 to 98%, more preferably 20 to 80%, particularly 20 to 50% by weight. Additional components may include a glycol mono- or di-ether, e.g. a mono- or di-ether of one or more of the glycols listed earlier in the specification. The ethers are suitably $C_1$ to $C_{10}$ alkyl ethers, particularly lower alkyl ($C_1$ to $C_6$) ethers, e.g. ethyl ethers and are preferably $C_1$ to $C_4$ alkyl ethers of di-, tri-, or tetra-ethylene, propylene or butylene glycols. The glycol ether component may be present in a concentration in the range 2 to 95% by weight, preferably 20 to 80% by weight.

The hydraulic fluid may also contain a minor amount, e.g. up to 20%, preferably up to 10% of a polyglycol, e.g. polyethylene glycol. The polyglycol has a molecular weight greater than 150 and preferably in the range 150 to 400.

Other components of the hydraulic fluid which may be present in smaller concentrations include pH control and corrosion inhibitors such as an alkali metal borate, an amine such as an ethanolamine or $C_4$ to $C_{14}$ alkylamine, a morpholine, mercaptobenzotriazole, benzotriazole, or a nitrite such as sodium nitrite; and an antioxidant e.g. a hindered phenolic antioxidant such as 2,4-dimethyl-6-tert.butylphenol or 4-methyl-2,6-ditert.butylphenol, phenothiozine or a substituted phenylene diamine. Such additives which may be used in concentrations up to 5% by weight of the fluid are only a selection of those known for this purpose and many equally as suitable will be known to those skilled in the art.

We have found that hydraulic fluid compositions in accordance with the present invention are advantageous in as much as the presence of a glycol residue C in the borate ester gives improved, i.e. lower, rubber swell properties and also improved lubricating properties as compared with borate esters in which C as well as A is a glycol ether residue.

The compositions according to the invention will now be further described with reference to the following Example.

EXAMPLE

(A) Preparation of Borate Ester 1 mole of boric acid and 1 mole of tetraethylene glycol were heated together at 100° C. until the calculated amount of water had been removed. The reaction mixture was then cooled down and 2 moles of triethylene glycol mono-ethylether added. The esterification was then recommenced and continued at 100° C. until the required amount of water had been removed.

(B) Evaluation of a Hydraulic Fluid Composition

The borate ester produced as in (A) was made up into a hydraulic fluid composition containing:

| | By Weight |
|---|---|
| Borate ester | 30.0% |
| Mixed ethers comprising diethylene glycol, monoethyl ether (34.2% w/w), triethylene glycol monoethyl ether (34.59% w/w), tetraethylene glycol monoethyl ether (21.8% w/w), pentaethylene glycol monoethyl ether (7.7% w/w), and hexamethylene glycol monoethyl ether (1.8% w/w) | 69.5% |
| 2,4-dimethyl-6-tert.butylphenol | 0.3% |
| Diethanolamine | 0.1% |
| Benzotriazole | 0.1% |
| Sodium Nitrite | 0.025% |

This composition was evaluated against a brake fluid specification DOT4 published by the U.S. Department of Transport. The results of the tests included in this specification were as follows:

| Test | Result |
|---|---|
| Dry equilibrium boiling point °C. | 247 |
| Wet equilibrium boiling point °C. | 165 |
| Viscosity(cs) at −40° C. | 1104 |
| pH | 7.8 |
| Reserve alkalinity (mls. $N/10$ hydrochloric acid) | 7.9 |
| High temperature stability °C. | −3 |
| Chemical stability °C. | −2 |
| Fluidity (secs.) at −50° C. | 6 |
| Evaporation % wt/wt | 61.4 |
| Water tolerance at −40° C. (secs.) | 5 |
| Water tolerance at 60° C. | Pass |
| Compatability at −40° C. | Pass |
| Compatability at 60° C. | Pass |
| Effect on SBR rubber cups | 0.466/8° |

(mm diameter increase at 120° C. and decrease in hardness in International Rubber Hardness Degrees).

Finally, the wet fluid was tested to discover at what temperature vapour started to form in the liquid. This was found to be 157° C. (the fluid was humidified as described in Section 6.2.1 of the DOT4 Rules and Regulations).

EXAMPLE 2

(a) 1.5 moles of orthoboric acid and 1.5 moles tetraethylene glycol were heated together up to 100° C. and a quantity of water, equivalent to that which would be produced from esterification of one hydroxy group, was removed. The reaction mixture was then cooled and 3 moles of a glycol ether mixture (average M.W. 218) were added. The glycol ether mixture had been produced by random cc. alkoxylation of diethylene glycol monoethyl ether with a mixture of 40% by weight ethylene and 60% by weight propylene oxides. After allowing time for thorough mixing the esterification was continued by heating up to 155° C. and a further quantity of water was removed equivalent to the number of moles of glycol ether. The product obtained had the following properties at 25° C:

| Density grams/ml. | : | 1.0636 |
| --- | --- | --- |
| Viscosity Cp | : | 70.6 |
| $n_D$ 25° C. | : | 1.4475 |
| Equilibrium Reflux boiling pt. °C. | : | 303 |

(b) A hydraulic fluid containing 40% by volume of this ester and 60% by volume of the same glycol esters as were used in the preparation of the borate ester, had the following properties:

| Reflux boiling pt. °C. | : | 268 |
| --- | --- | --- |
| Viscosity at −40° C. cs. | : | 2104 |

EXAMPLE 3

(a) 1.5 moles ortho boric acid and 1.5 moles diethylene glycol were heated together until the quantity of water removed was equivalent to that produced from the esterification of one hydroxyl group. The reaction mixture was cooled and 3 moles of the mixed glycol ethers described in Example 2 were added. Following the same procedure as in Example 2 the reaction was continued by heating up to 145° C. The product obtained had the following properties at 25° C:

| Density grams/ml. | : | 1.0555 |
| --- | --- | --- |
| Viscosity cp. | : | 53.8 |
| $n_D$ 25° C. | : | 1.4446 |
| Reflux boiling pt. °C. | : | 301 |

(b) A hydraulic fluid containing 40% by volume of this ester and 60% by volume of the glycol ethers described in Example 2 had the following properties:

| Reflux boiling pt. °C. | : | 265 |
| --- | --- | --- |
| Viscosity at −40° C. cs | : | 1901. |

I claim:

1. A hydraulic fluid which comprises an ester of orthoboric acid of general formula

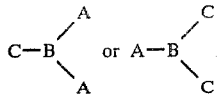

where C is a radical of a glycol containing up to 30 carbon atoms or a polyglycol containing 2 to 20 ethylene and/or propylene oxide units selected from the group consisting of polyethylene glycol, polypropylene glycol and a polyglycol derived from mixed ethylene oxide and propylene oxide units, B is a boron atom and A is a glycol ether radical in which the glycol is as defined for C etherified with a $C_1$ to $C_{20}$ alkyl group.

2. A hydraulic fluid as claimed in claim 1 in which C is derived from ethylene, propylene or butylene glycol, neopentyl glycol or a polyethylene or polypropylene glycol or a glycol derived from mixed ethylene oxide/propylene oxide units.

3. A hydraulic fluid as claimed in claim 1 in which A is derived from an ether of ethylene, propylene or butylene glycol, neopentyl glycol, polyethylene glycol, polypropylene glycol or a glycol derived from mixed ethylene oxide/propylene oxide units.

4. A hydraulic fluid as claimed in claim 1 in which the ester of orthoboric acid comprises 5 to 98% by weight of the fluid.

5. A hydraulic fluid as claimed in claim 1 which also comprises a glycol mono- or di-ether.

6. A hydraulic fluid as claimed in claim 5 in which the glycol ether is derived from a glycol which is ethylene, propylene or butylene glycol, neopentyl glycol, polyethylene glycol, polypropylene glycol or a glycol derived from mixed ethylene oxide/propylene oxide units.

7. A hydraulic fluid as claimed in claim 1 which comprises a polyglycol with a molecular weight greater than 150.

8. A hydraulic fluid as claimed in claim 1 which includes a pH control and corrosion inhibitor and/or an antioxidant.

9. A hydraulic fluid as claimed in claim 1 in which
(a) C is derived from a polyethylene or polypropylene glycol or a glycol derived from mixed ethylene oxide/propylene oxide units, the polyglycol containing 2 to 6 repeating ethylene oxide and/or propylene oxide units,
(b) A is derived from a $C_1$ and $C_6$ alkyl ether of a glycol defined as in (a),
(c) the fluid comprises 20 to 80% by weight of said ester of orthoboric acid,
(d) the fluid also comprises 20 to 80% by weight of a $C_1$ to $C_6$ alkyl mono- or di-ether of di-, tri- or tetra-ethylene, propylene or butylene glycol.

10. Hydraulic fluid consisting essentially of:
(1) about 5 to 98% by weight of a borate ester having the formula:

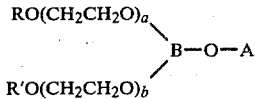

wherein each of a and b is an integer having values of 2 to 6, each of R and R' is an alkyl group having 1 to 6 carbon atoms, and A is an oxyalkylene unit, including mixed oxyalkylene units, having the formula:

$-(C_nH_{2n}O)_x-H$ wherein n is 2 or 3 and x is an integer having values of 1 to 6;

(2) 0 to 80% by weight of a monoalkoxy trialkylene glycol having the formula:

$H-(OCH_2CHR'')_3-OR'''$ wherein R''' is an alkyl group having 1 to 4 carbon atoms and R'' is H or —CH$_3$ and (3) 0 to 80% by weight of a monoalkyl ether of diethylene glycol wherein the alkyl group contains 1 to about 4 carbon atoms.

11. Hydraulic fluid claimed in claim 10 wherein a and b are each 4.

12. Hydraulic fluid claimed in claim 10 wherein a and b are each 2.

13. Hydraulic fluid claimed in claim 11 wherein n is 2 and x is 4.

14. Hydraulic fluid claimed in claim 12 wherein n is 2 and x is 4.

15. Hydraulic fluid claimed in claim 10 wherein the amount of boric acid ester is about 20 to about 80% by weight.

* * * * *